United States Patent [19]
Kessler et al.

[11] Patent Number: 5,600,068
[45] Date of Patent: Feb. 4, 1997

[54] CONTROLLED-IMMERSION INSPECTION

[75] Inventors: Lawrence W. Kessler, Buffalo Grove; Daniel M. Erickson, Schiller Park; Daniel W. Micek, Norridge; John Billone, DesPlaines, all of Ill.

[73] Assignee: Sonoscan, Inc., Bensenville, Ill.

[21] Appl. No.: 515,601

[22] Filed: Aug. 16, 1995

[51] Int. Cl.$^6$ ............................................. G01N 29/26
[52] U.S. Cl. ............................................. 73/620
[58] Field of Search ........................ 73/620, 629, 644, 73/633, 582, 592, 41.2, 41.3, 41.4, 45.5, 148; 324/501, 514

[56] References Cited

U.S. PATENT DOCUMENTS 5,359,895  11/1994  Isenberg et al. .................... 73/592

*Primary Examiner*—John E. Chapman
*Attorney, Agent, or Firm*—Dorn, McEachran, Jambor & Keating

[57] ABSTRACT

A controlled-immersion inspection mechanism gradually immerses a planar pattern of integrated circuits or other articles into a tank filled with water to a given level; across the tank there are two spaced parallel guide tracks along which two carriages, connected by a platform, move from an entry position above the water to an inspection position. In the inspection position the platform supports the articles, in an orderly array, for scanning inspection by a focussed energy beam, preferably an ultrasonic beam. A platform drive drives the platform between its entry and inspection positions. A mesh or other removable cover that permits water to flow but stabilizes article positions may cover the articles during immersion; the mesh is usually removed before scanning.

20 Claims, 6 Drawing Sheets

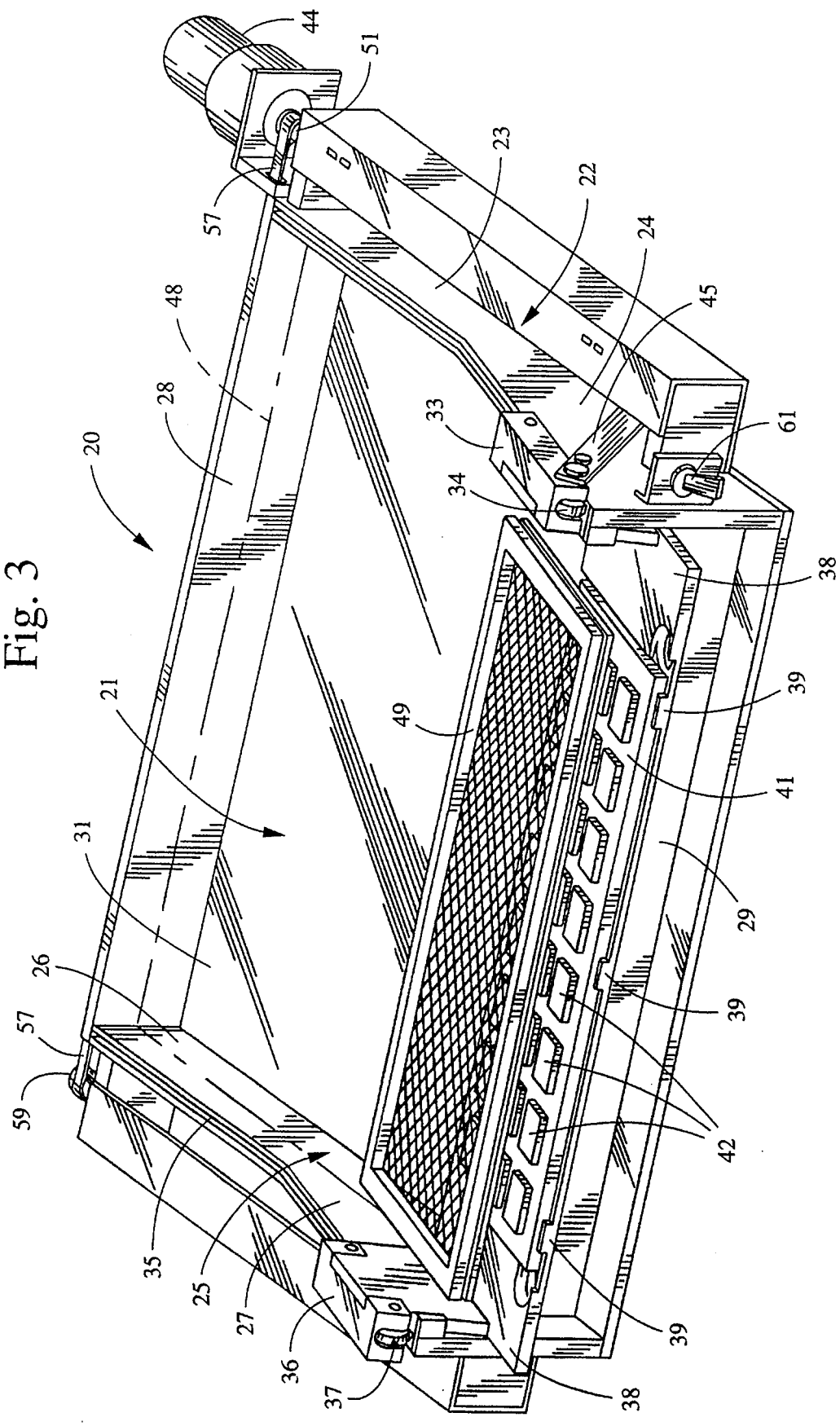

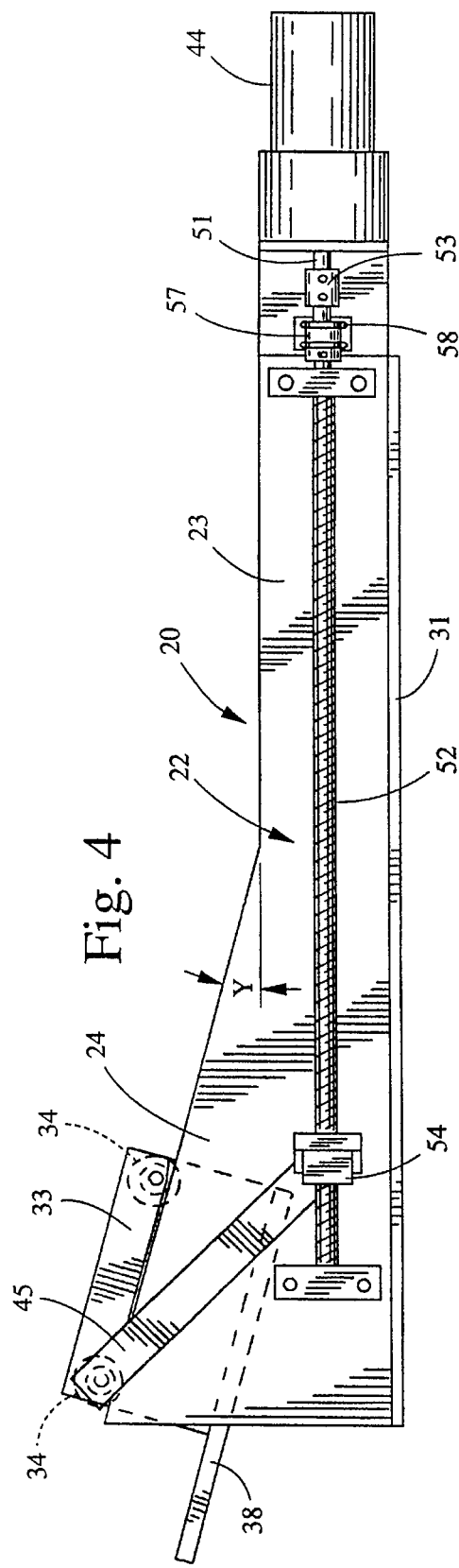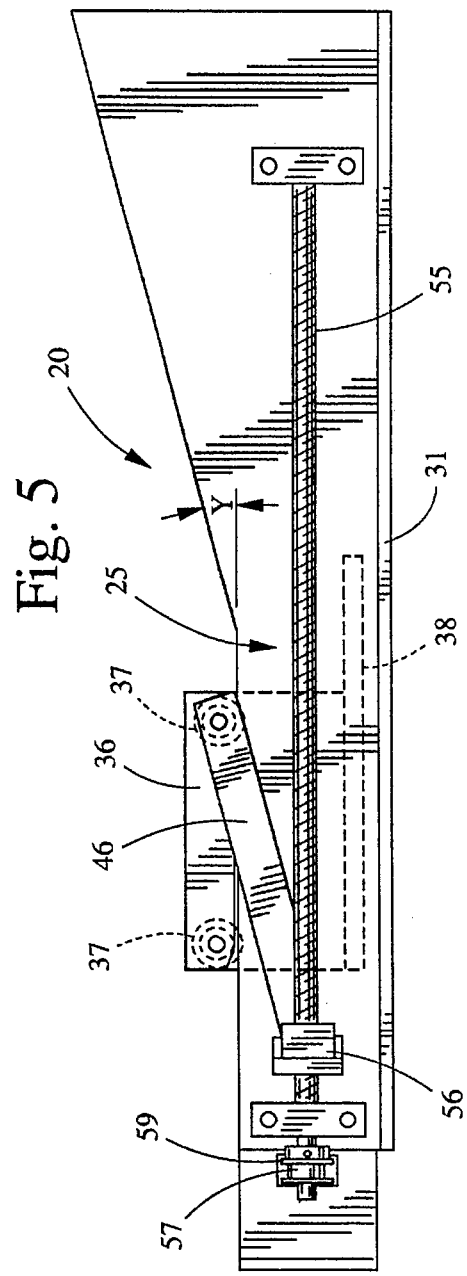

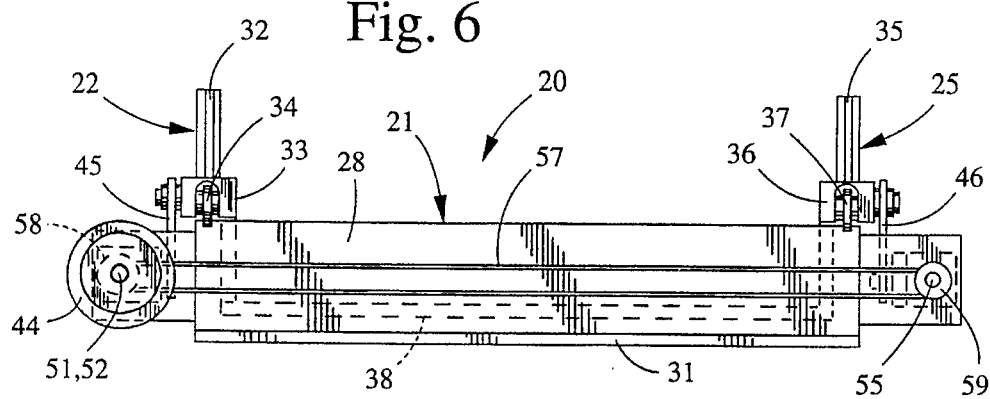
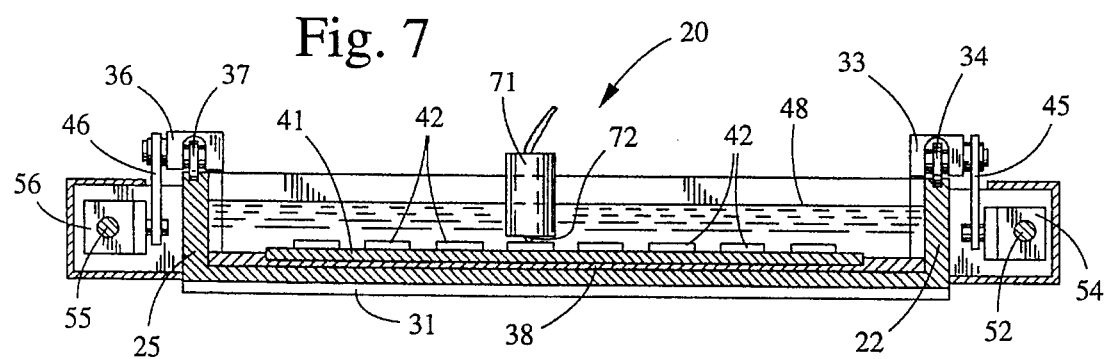
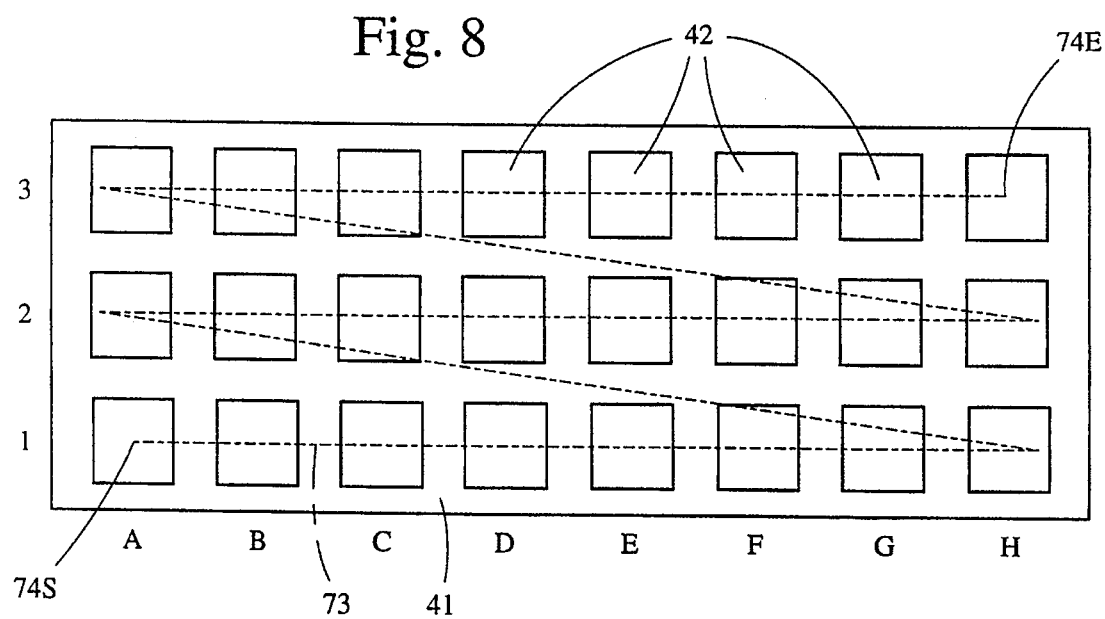

CONTROLLED-IMMERSION INSPECTION

BACKGROUND OF THE INVENTION

With the growing and continued use of an increasingly broad variety of electronic devices in both commercial and industrial applications, the manufacturers of such devices are producing ever increasing numbers of articles. Furthermore, the variety of those electronic articles (integrated circuits, transistors, capacitors, etc.) continues to grow. Demands of users for higher quality and reliability have imposed increasingly greater requirements for more extensive and comprehensive inspection of these electronic components. Indeed, for some applications, one hundred percent inspection is a common requirement. Of course, any such inspection must be non-destructive with respect to the articles themselves.

One of the widely accepted methods for non-destructive testing of integrated circuits, transistors, capacitors, and other electronic components utilizes a scanning acoustic microscope. However, inspection by acoustic microscopy is frequently a relatively slow process, particularly as compared with other test procedures directed to inspection of the electronic functions of the devices. As a consequence, it is highly desirable to have an inspection mechanism with the capability of testing a substantial variety of electronic articles in an automated procedure. Even so, there are a number of problems that to be overcome in the utilization of acoustic microscopy for inspection procedures, particularly because inspection with an acoustic microscope usually requires that the article being inspected be immersed in water or some other liquid inspection medium during testing.

For many electronic components, particularly integrated circuits, the articles requiring inspection should be inspected while still in trays. Encapsulated integrated circuits and other like electronic articles can be loaded into trays, in orderly patterns, using trays that are especially designed to hold articles of a specific type. Typically, the test articles are arranged in a grid pattern of rows and columns. Often, the articles are packaged loosely in trays. The electronic leads of these electronic devices are often quite delicate, so that any handling may present a substantial problem. Often, the articles to be inspected are not secured in trays or other like supports, so that introduction of the articles into water or some other liquid test medium may cause some of the parts to float, usually due to surface tension of the liquid. Moreover, air bubbles may collect on top of and underneath the articles at the time of immersion.

SUMMARY OF THE INVENTION

It is an object of the present invention, therefore, to provide a new and improved mechanism and method for immersing electronic articles (integrated circuits, transistors, capacitors, ceramics etc.) in water or a like liquid test medium without substantially altering or disturbing a predetermined pattern of the articles to be inspected.

Another object of the invention is to provide a new and improved controlled-immersion mechanism and method for immersing a predetermined pattern of electronic articles in a liquid medium at a controlled speed and angle, simultaneously minimizing bubble collection and any tendency on the part of the articles to float. For very small or light-weight articles, a mesh or other open cover is placed over the articles; the mesh serves to keep the articles in place during their immersion. Simultaneously, the array of articles (usually on a tray) may be jogged while being introduced into the liquid medium, even after the articles have actually been immersed. Gradual withdrawal of the articles from the liquid inspection medium serves to control drainage of the liquid from the articles and to preserve the pattern of the articles without material change so that they are more readily packaged for shipment to users.

Accordingly, in its apparatus aspect this invention relates to a controlled-immersion inspection mechanism to immerse plural articles arranged in an orderly pattern into a tank filled to a given level with a liquid medium. The controlled-immersion inspection mechanism comprises a tank, first and second guide tracks extending across the tank in parallel spaced relation to each other, each guide track including an inspection segment parallel to the given level of the liquid and an entry segment extending upwardly at an acute angle from one end of the inspection segment, with first and second carriages movable along the first and second guide tracks, respectively. A platform extends between the first and second carriages, for supporting plural articles arranged in an orderly pattern for inspection; a platform drive is connected to the platform for driving the platform between an entry position, in which the articles are elevated above the given level, and an inspection position, in which the articles are immersed in the liquid medium at a predetermined level below the given level.

In its method aspect the invention relates to a method of inspecting a plurality of articles comprising the steps of:

A. filling a tank to a given level with a liquid medium;
B. arranging the articles in an orderly planar pattern;
C. moving the planar pattern of articles into the tank, along a path at an acute angle to the given liquid surface level, from an entry position above the given level to an inspection position in which the pattern of articles is immersed in the liquid medium, parallel to but at a predetermined level below the given level; and
D. scanning the articles, in the inspection position, with a beam of scanning energy, in accordance with a preselected scanning pattern correlated with the planar pattern of the articles.

BRIEF DESCRIPTION OF THE DRAWINGS

FIG. 3 is a perspective view like FIG. 1 but with an additional mesh member;

FIG. 4 is a side elevation view of the right-hand side of the mechanism in the position of FIG. 1, with covers removed to show a part of the platform drive;

FIG. 5 is a side elevation view like FIG. 4 but showing the platform drive from the left-hand side, in the inspection position of FIG. 2;

FIG. 6 is a rear elevation view of the mechanism in the position of FIG. 2;

FIG. 7 is a partly schematic section view taken approximately along line 7—7 in FIG. 2;

FIG. 8 is a schematic illustration of a typical article array for inspection;

DESCRIPTION OF THE PREFERRED EMBODIMENTS

Figure 1:
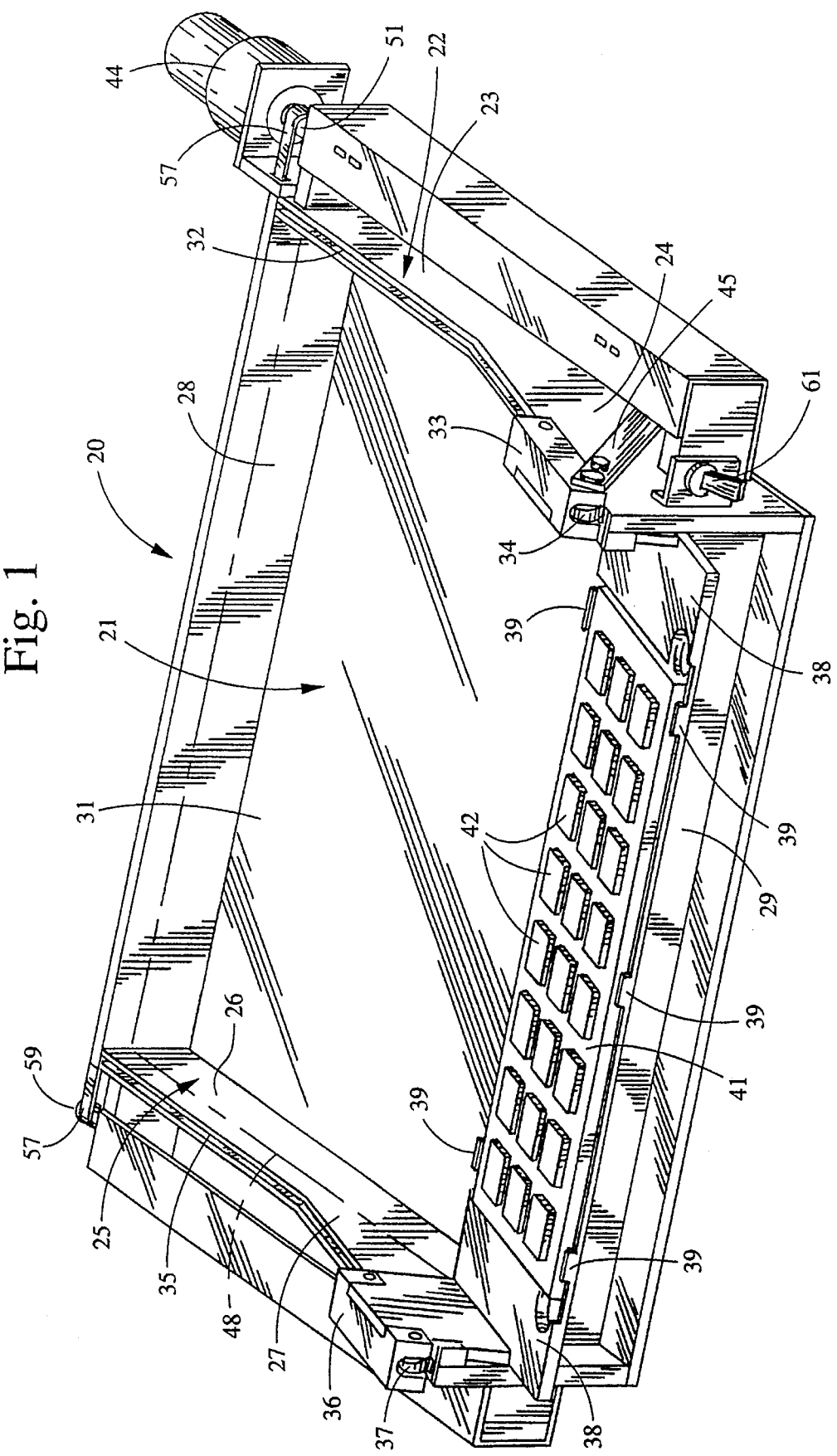
FIG. 1 is a perspective view of a controlled-immersion inspection mechanism constructed in accordance with a preferred embodiment of the invention, with the mechanism in its start or entry position.
Figure 2:
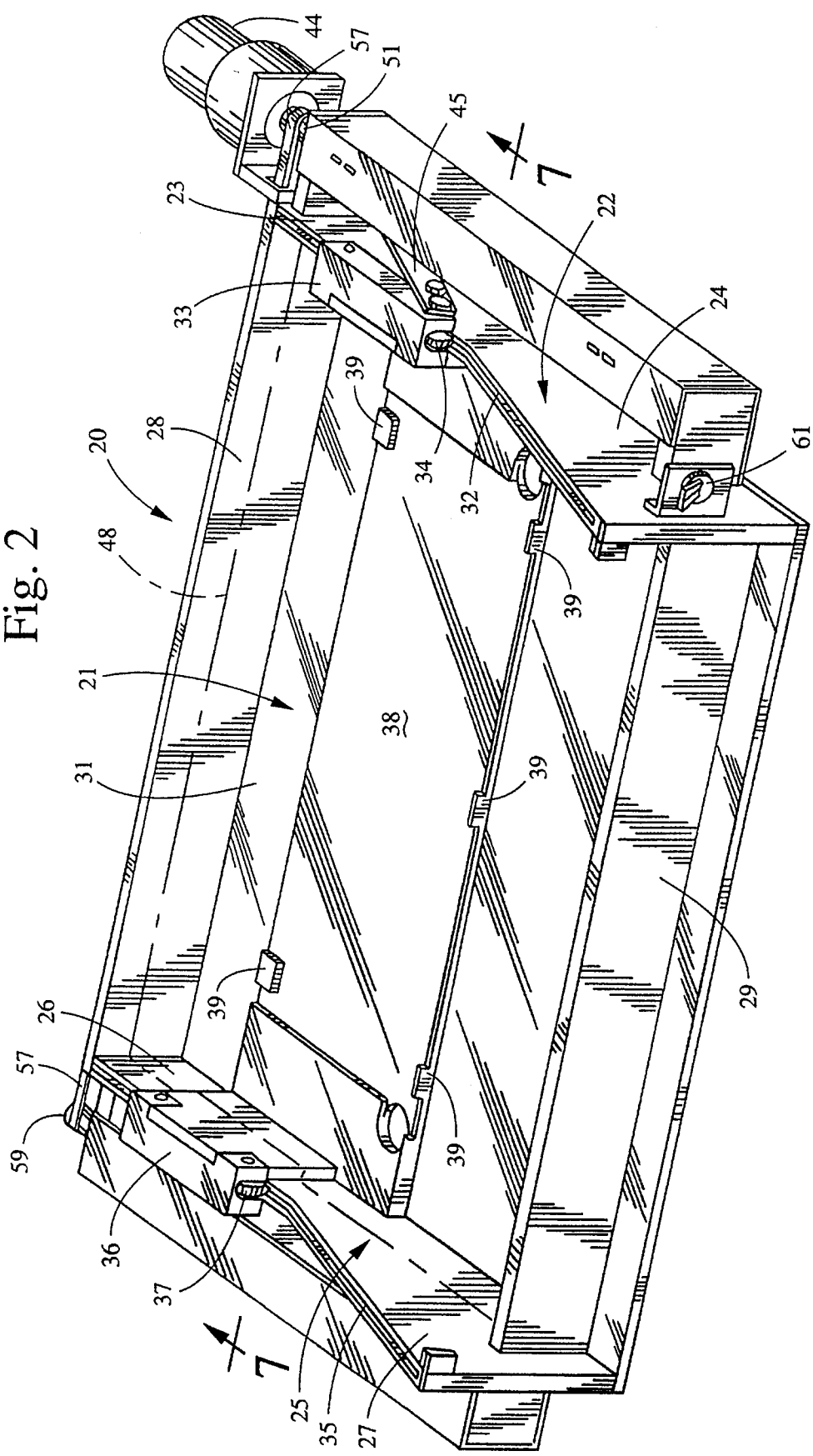
FIG. 2 is a perspective view like FIG. 1 but with the mechanism in its immersed inspection position.

FIGS. 1 and 2 illustrate a controlled-immersion mechanism 20 constructed in accordance with a preferred embodiment of the present invention. In FIG. 1 mechanism 20 is shown in its "start" or entry position. FIG. 2 shows the same controlled-immersion mechanism 20 in its immersed or inspection position.

Controlled-immersion mechanism 20 includes a tank 21 having a right-hand side wall 22. Side wall 22 of tank 21 includes an inspection segment 23 from which an entry/withdrawal segment 24 extends upwardly at an acute angle. That angle is typically in a range of thirty to ten degrees, depending on the surface tension of the test fluid; see FIGS. 4 and 5, angle Y. The other left-hand side wall 25 of tank 21 also has a rear or inspection segment 26 of uniform height from which an entry/withdrawal segment 27 extends, again at an acute angle. Tank 21 also includes a rear wall 28, a front wall 29, and a bottom 31. Tank 21 should be water tight and is filled with water or a comparable liquid test medium to a predetermined level indicated, in FIGS. 1 and 2, by the phantom line 48.

The upwardly-facing top edge of tank wall 22 includes an elongated groove 32. Groove 32 extends throughout the full length of tank wall 22, including both wall segments 23 and 24, and constitutes a first guide track for a first carriage 33. Carriage 33 is provided with a pair of guide wheels 34 that engage in track 32 so that the carriage is compelled to follow the track during operation of controlled-immersion mechanism 20, a described more fully hereinafter. At the other side of tank 21 wall 25 is provided with a similar groove or guide track 35 for a second carriage 36 that is mounted upon a pair of carriage rollers 37. That is, carriage rollers 37 engaged in guide track 35 and guide the movements of carriage 36 along the top of the tank side wall 25. An elongated platform 38 extends across tank 21 between carriages 33 and 36; platform 38 is suspended from the two carriages. Platform 38 is provided with a series of stops or location members 39 along its front and rear edges to provide for accurate positioning of a tray 41 on the platform. Tray 41 supports a plurality of articles 42 that are to be tested in mechanism 20; tray 41 and articles 42 have been omitted in FIG. 2 so that the immersion position for platform 38 is more clearly illustrated.

A platform drive motor 44 is mounted on a suitable bracket at the right-hand rear of mechanism 20, as illustrated in FIGS. 1 and 2. Motor 44 is connected, by two drive links 45 and 46 and a drive belt 57, to the platform supports, in this instance the carriages 33 and 36. A mesh or screen member 49 having the same size and shape as tray 41 may be positioned over articles 42, as shown in FIG. 3, when necessary.

Controlled-immersion mechanism 20 further includes a drive platform 38, driven by motor 44; the platform drive is best illustrated in FIGS. 4–6. As best shown in FIG. 4, which illustrates the right-hand side of mechanism 20 with some of the sheet metal covers removed, the shaft 51 of motor 44 is connected through a coupler 53 to a first elongated lead screw 52. Lead screw 52 extends parallel to tank wall 22 and is almost as long as the tank side wall. A lead screw drive nut or follower 54 is mounted in threaded encompassing relation to lead screw 52 and is pivotally connected to one end of drive link 45, the other end of the drive link being pivotally connected to carriage 33.

The portion of the platform drive on the opposite side of mechanism 20 is illustrated in FIG. 5. It includes an elongated lead screw 55 that extends parallel to tank side wall 25 for most of the length of the tank wall. A second drive nut 56 is disposed in encompassing threaded relation to lead screw 55 and is pivotally connected to one end of drive link 46. The other end of drive link 46 is pivoted to the second carriage 36 of mechanism 20. Lead screw 55 is driven from motor 44 by a drive belt 57 that extends across the rear of mechanism 20; see FIG. 6. Belt 57, which is usually a timing belt, engages a first pulley 58 mounted on one end of lead screw 52 and rotate with the lead screw 52. A second pulley 59 is mounted on the rear end of lead screw 55.

In operation, the controlled-immersion inspection mechanism 20 of the invention requires that tank 21 be filled with a liquid medium to a given level, as indicated by level 48 in FIGS. 1–3. In most instances, and particularly when scanning acoustic microscopy is to be utilized for inspection, mechanism 20 is an integral part of a scanning acoustic microscope. The electronic components or other articles 42 to be tested are arranged in an orderly planar pattern, usually on a tray 41, as shown in FIGS. 1 and 3. Tray 41 may be magnetic, to hold articles 42 in place. Other arrangements for accurate location of articles 42 in a predetermined pattern are acceptable. The usual pattern for articles 42 is a raster pattern of rows and columns as best shown in FIGS. 1 and 8. The electronic circuits or other articles to be inspected may be deposited directly upon platform 38, if desired, but the more common practice is to arrange the inspection articles on a tray, such as tray 41, at some location apart from mechanism 20; the tray is then disposed on platform 38 and is held in the desired position by stops 39.

At this juncture, in practicing the method made possible by mechanism 20, platform 38 is driven from the entry position illustrated in FIGS. 1, 3 and 4, above the liquid level 48 in tank 21, to the inspection position illustrated in FIGS. 2, 5 and 6. For this movement, from the entry position to the inspection position, it is highly desirable to move the platform and the articles that it bears at an acute angle to the surface level of the liquid in tank 21. This acute angle, angle Y (FIGS. 4 and 5), gradually immerses the articles 42 in the liquid in the tank so that the liquid does not displace the articles from the original orderly pattern best shown in FIGS. 1 and 8. The requisite movement of platform 38 from the position shown in FIG. 4 to the position illustrated in FIG. 5 is effected by operation of motor 44 and the platform drive comprising the lead screws 52 and 55. Thus, motor 44 rotates lead screws 52 and 55 appropriately to move their followers or drive nuts 54 and 56 from a position adjacent the front of the mechanism (FIG. 4) to a position near the rear of the mechanism (FIG. 5). The movement of the two drive nuts 54 and 56 along their respective lead screws 52 and 55 pulls carriages 33 and 36 along tracks 32 and 35, respectively, ending up with the mechanism in the inspection position of FIGS. 2, 5 and 6 with articles 42 parallel to but at a predetermined level below the water level 48. This inspection position is best illustrated in FIG. 7.

With the pattern of articles 42 to be inspected in the inspection position of FIG. 7, the articles are scanned with a beam 72 of scanning energy, in accordance with a preselected pattern correlated with the pattern of the articles 42. Beam 72 is developed by an appropriate transducer 71. In a scanning acoustic microscope transducer 71 emits a focused beam of ultrasonic energy, usually in the range of ten to one hundred megahertz. The scanning pattern may be as illustrated by phantom line 73 in FIG. 8, which affords a plan view of tray 41 and articles 42. Two or more scans may be carried out. For example, one scan, starting at point 74S and ending at point 74E, may be utilized to examine the bond between the package material and the die surface of an encapsulated integrated circuit chip, in those circumstances in which each of articles 42 constitutes such an encapsulated integrated circuit. A second scan of the same articles may focus on the die area. Each scan can have its own set of parameters, with gating to concentrate on the desired area of each article 42. Furthermore, the depth of focus may change for each scan. Indeed, the user of mechanism 20 can set up a custom analysis package for each scan, depending upon the articles 42 being inspected, to make use of histograms, pixel counting, determination of corner voids, or any other analysis feature available with the particular scanning acoustic microscope in which the controlled-immersion inspection mechanism 20 is incorporated. For a scanning inspection utilizing a scanning pattern of the kind illustrated by phantom lines 23 in FIG. 8, the end result is an output signal from transducer 71 to indicate whether the article is acceptable or should be rejected. The following is a typical output from a two-scan inspection:

TABLE I (0 = OK; X = Reject)

| Article Position | First Scan | Second Scan | Article Status |
| --- | --- | --- | --- |
| 1A | 0 | X | Reject |
| 1B | 0 | X | Reject |
| C | 0 | 0 | Accept |
| D | 0 | 0 | Accept |
| E | 0 | 0 | Accept |
| F | 0 | 0 | Accept |
| G | 0 | 0 | Accept |
| H | 0 | 0 | Accept |
| 2A | 0 | 0 | Accept |
| 2B | 0 | 0 | Accept |
| C | 0 | 0 | Accept |
| D | 0 | X | Reject |
| E | 0 | 0 | Accept |
| F | 0 | 0 | Accept |
| G | 0 | 0 | Accept |
| H | 0 | X | Reject |
| 3A | 0 | 0 | Accept |
| 3B | X | — | Reject |
| C | X | — | Reject |
| D | X | — | Reject |
| E | 0 | 0 | Accept |
| F | 0 | 0 | Accept |
| G | 0 | 0 | Accept |
| H | 0 | 0 | Accept |

In carrying out the scanning inspection, when the tray or other support for the pattern of articles 42 to be tested is in the inspection position, the first step is to locate the first part in position 1A (FIG. 8 and Table I). Next, the transducer 71 is focused on the top of the article 42 occupying position 1A and is moved to the desired location, usually the center, of the part. This may be done only once for each pattern of articles inspected, in order to establish the location of the first part at the position 1A on the tray. All of the other articles 42 may be indexed according to the dimensions of the article pattern and the pattern itself.

Ordinarily, scanning inspection may continue from one article to another as long as there is an article in place where one can be expected in the pattern. In the event that the article for a given position in the pattern is missing, or in circumstances in which a portion of the pattern is not completely populated with articles, the scan software of the acoustic microscope can determine that an article is missing and skip that location, continuing on until all articles have been scanned and analyzed. From the time the scanning and analysis process is begun until it is finished, an estimated time to completion is often displayed. Of course, the number of rows and columns for the pattern of articles 42 need not conform to FIG. 8, which is shown only as an example, the pattern will depend on the size of articles 42 and other like factors.

After the scanning inspection, articles 42 need to be removed from the tank, to some withdrawal position above the surface level 48 for the liquid medium in the tank, for packaging and shipment. Mechanism 20 should also be prepared for the next inspection operation. The most expedient way of doing this, with mechanism 20, is simply to reverse motor 44 and move platform 38 back out to the entry position of FIG. 1, which now becomes a withdrawal position for the platform and articles 42. With platform 38 back in the position of FIG. 1, it is then a simple matter to remove tray 41 or to remove articles 42 individually, thereby establishing mechanism 20 in condition for the next inspection operation.

As previously pointed out, test articles 42 may be so small or light in weight that they may tend to float as they move into the liquid test medium in tank 21, depending on the surface tension of the liquid. Floating cannot be tolerated because it disturbs the pattern or test articles on platform 38, regardless of whether there is or is not a tray 41 interposed between the articles to be inspected and the platform. For inspection of such small or light-weight articles, the mesh member 49 of FIG. 3 is employed. Before the controlled-immersion inspection mechanism 20 is energized, the mesh or screen member 49 is placed over the articles 42 to be inspected. The mesh area of member 49 should be large enough to encompass the entire pattern of test articles 42. The mesh or screen member 49 remains in place during immersion of platform 38 and its cargo of test articles 42 in their predetermined pattern. This serves to keep the articles in place and in their predetermined pattern while they are being introduced into the water in tank 21. The mesh member 49 is usually lifted from the articles, prior to carrying out the inspection procedure. If the mesh of member 49 has openings that coincide with the edges of the articles being tested, it may remain in place during the scanning operation. Also, to avoid any tendency toward accumulation of air bubbles either over or under articles 42, it is preferable that platform 38 be jogged, usually in a forward and backward direction, as it moves downwardly into the water or other liquid medium in tank 21.

Figure 9:
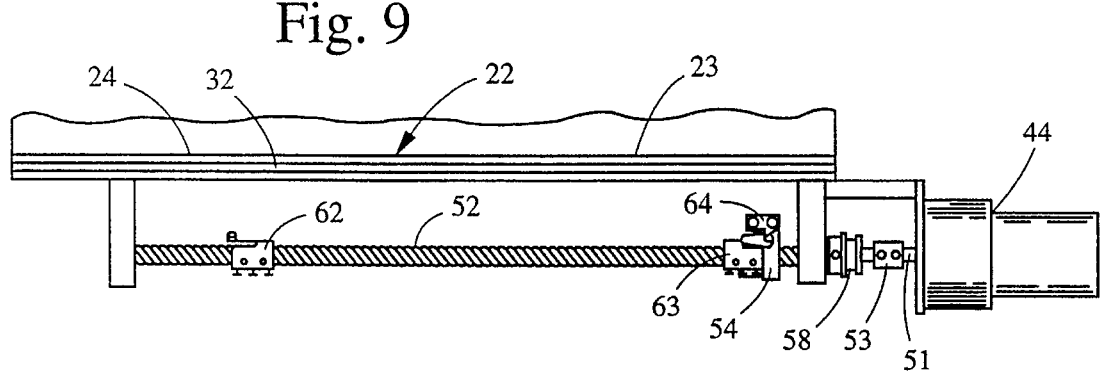
FIGS. 9 and 10 are simplified plan and elevation views, respectively, of the right-hand side of the inspection mechanism, used to show typical limit switch locations for control of the immersion mechanism.
Figure 10:
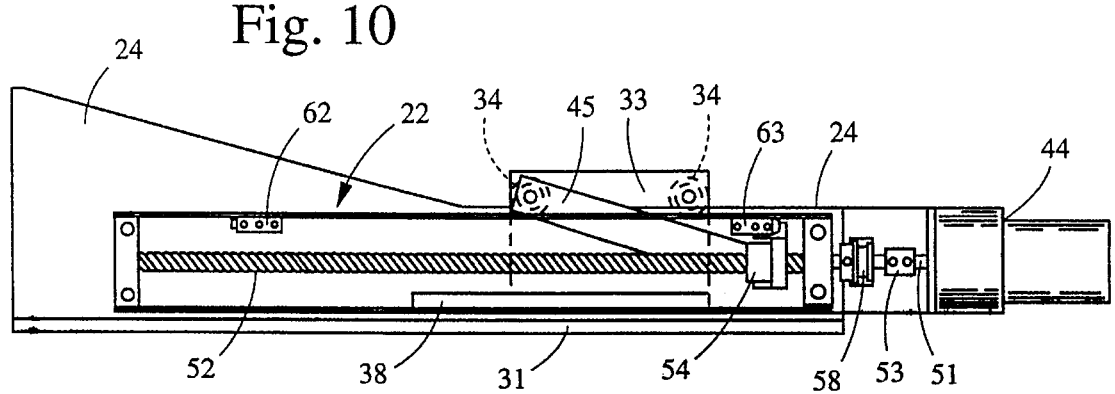
Figure 11:
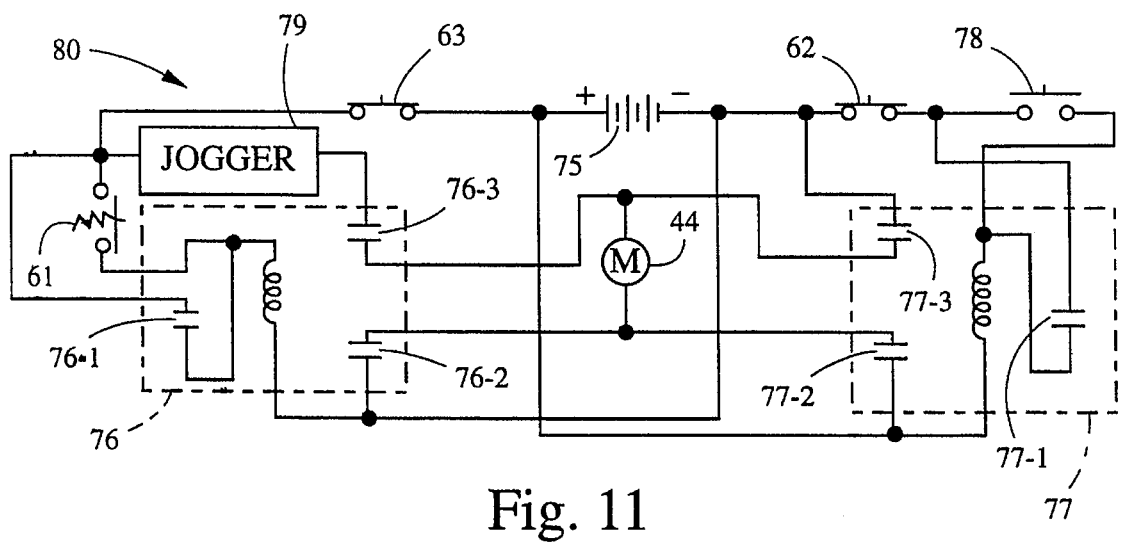
FIG. 11 is a simplified circuit diagram of a control circuit for the immersion mechanism drive.

FIG. 11 is a schematic circuit diagram of an energizing circuit for motor 44 that may be employed in operation of the controlled-immersion inspection mechanism 20. It will be recognized that the operating circuits shown in FIG. 11 are exemplary only and can be varied to suit requirements of the controlled-immersion mechanism or of the scanning acoustic microscope or other inspection equipment in which that mechanism is incorporated. FIGS. 9 and 10 illustrate limit switches that also appear in FIG. 11 and that signal movement of platform 38 from its entry position (FIG. 1) to its inspection position (FIG. 2) and withdrawal back to the entry location.

As shown in FIGS. 9 and 10, there are two limit switches 62 and 63 for the control circuits shown in FIG. 11. Limit switch 62 is positioned near the front of the controlled-immersion inspection mechanism and may be mounted on segment 24 of tank side wall 22 in position to be engaged by platform 38 or by the carriage 33 that supports one end of the platform. Limit switch 63, on the other hand, is mounted at the rear end of the tank in position to be engaged by a limit switch actuator 64 that is secured to the drive nut 54 on lead screw 52. Actuator 64 appears in FIG. 9.

The electrical operating circuit 80 illustrated in FIG. 11 comprises a power source, shown as a battery 75. The positive terminal of battery 75 is connected to motor 44 through limit switch 63, a jogger circuit 79, and one pair of normally open contacts 76-3 of a first relay 76. The other terminal of motor 44 is returned to the negative terminal of battery 75 through another set of normally open contacts 76-2 of relay 76. The positive terminal of battery 75 is also connected to the operating coil of relay 76 through the on-off switch 61 located at the front of the mechanism as shown in FIGS. 1–3. The operating coil of relay 76 is returned directly to the negative terminal of battery 75. Another set of normally open contacts 76-1 in relay 76 is connected in parallel with switch 61.

The foregoing portion of circuit 80 is shown at the left-hand side of FIG. 11. At the right-hand side of the circuit, as illustrated in FIG. 11, the negative terminal of battery 75 is connected to the operating coil of a relay 77 through the series combination of limit switch 62 and a program connection illustrated as a normally-open switch 78. The coil of relay 77 is returned to the positive terminal of battery 75 to complete the circuit. One set of normally open contacts 77-1 of relay 77 is connected in parallel with switch 78. Switch 78 is not actually a part of mechanism 21, when using circuit 11; instead, switch 78 represents a circuit connection that is completed in the controls for the inspection mechanism, such as the scanning acoustic microscope, in which the immersion mechanism 20 is incorporated. One terminal of motor 44 is connected to the negative terminal of battery 75 through normally open contacts 77-3 of relay 77. The other terminal of motor 44 is connected back to the positive side of battery 75 through another set of normally open contacts 77-2 of relay 77.

Movement of platform 38 from the initial loading or entry position illustrated in FIG. 1 to the immersion or inspection position illustrated in FIG. 2 is initiated by closing switch 61 momentarily; see FIG. 11. Closing switch 61 energizes the operating coil of relay 76 through a circuit starting at the positive terminal battery 75 and extending through limit switch 63 and switch 61 to the coil of the relay and then directly to the negative terminal of the battery. Thus, closing switch 61 energizes relay 76, with the result that its contacts 76-1, 76-2, and 76-3 all close. With the closing of these contacts, motor 44 is energized for initial or forward motion through a circuit starting at the positive terminal battery 75 and extending through limit switch 63, jogger circuit 79, relay contacts 76-3, motor 44, and relay contacts 76-2 to the negative terminal of the battery. Jogger circuit 79 serves to vary the amplitude of the energization to motor 44 to "jog" the motor (and platform 38) during immersion. The closing of contacts 76-1 maintains the coil of relay 76 energized even though switch 61 opens. Thus, motor 44 is energized for rotation in a direction to move platform 38 from the position of FIG. 1 to the position shown in FIG. 2.

When platform 38 reaches the inspection position of FIG. 2, it is desirable to de-energize motor 44 so that platform 38 will remain in the inspection position. When the platform attains its scanning or inspection position, limit switch 63 is actuated; the switch is opened. As a consequence, relay 76 drops out and all of its contacts open. Motor 44 is de-energized, leaving platform 38 in the position shown in FIG. 2. Scanning (inspection) of articles 42 thus can be carried out with platform 38 stationary.

When the inspection operation (FIGS. 7 and 8) is complete, "switch" 78 is closed momentarily by the controls of the inspecting apparatus in which mechanism 20 is incorporated. This establishes an energizing circuit for the operating coil of relay 77. Relay contacts 77-1, 77-2, and 77-3 all close. Accordingly, an operating circuit for motor 44 is completed, starting at the negative terminal of battery 75 and extending through relay contact 77-3 to motor 44 and then from the motor through relay contact 77-2 back to the positive terminal of the battery. This circuit is opposite in polarity to that previously employed, so that motor 44 is reversed and functions to drive platform 38 back to the original entry position (now a withdrawal position) illustrated in FIG. 1. During the withdrawal movement of platform 38, the relay 77 is held energized by its own contacts 77-1.

When platform 38 reaches the entry position of FIG. 1, limit switch 62 is opened. As a consequence, relay 77 is de-energized and its contacts all open. This effectively de-energizes motor 44 and the platform remains at the position shown in FIG. 1, ready for the next inspection operation as soon as the tray 41 of articles 42 is removed.

Many variations in the controlled-immersion mechanism 20 are permissible without departure from the invention. A different drive apparatus (e.g., a penumatic drive) may be utilized for platform 38, replacing lead screws 52 and 55 and drive links 45 and 46. Indeed, the platform drive may be connected directly to the platform. As previously noted, the exemplary control circuit 80 of FIG. 11 may be modified to meet requirements of inspection apparatus in which mechanism 20 is incorporated. The size of mesh member 49 (FIG. 3) may vary to meet requirements of different patterns of articles 42, which patterns are in turn dependent on the nature and size of the articles being inspected. However, platform 38 should introduce articles 42 into the liquid medium in tank 21 gradually; abrupt, vertical immersion is not satisfactory.

We claim:

1. A controlled-immersion inspection mechanism to immerse plural articles arranged in an orderly pattern into a tank filled to a given level with a liquid medium, the controlled-immersion inspection mechanism comprising:

a tank;

first and second guide tracks extending across the tank in parallel spaced relation to each other, each guide track including an inspection segment parallel to the given level and an entry segment extending upwardly at an acute angle from one end of the inspection segment;

first and second carriages movable along the first and second guide tracks, respectively;

a platform, extending between the first and second carriages, for supporting plural articles arranged in an orderly pattern for inspection;

and a platform drive, connected to the platform, for driving the platform between an entry position, in which the articles are elevated above the given level, and an inspection position, in which the articles are immersed in the liquid medium at a predetermined level below the given level.

2. A controlled-immersion inspection mechanism, according to claim 1, in which the platform drive is connected to the platform through at least one of the carriages.

3. A controlled-immersion inspection mechanism, according to claim 1, in which the platform drive is connected to the platform through both of the carriages.

4. A controlled-immersion inspection mechanism, according to claim 1, in which the platform drive comprises:

first and second elongated, threaded lead screws adjacent the first and second guide tracks, respectively;

first and second drive nuts threaded onto the first and second lead screws, respectively;

a rotary motor;

first and second drive linkages, connecting the motor to the first and second lead screws, respectively, to rotate the two lead screws simultaneously;

a first drive link pivoted at one end to the first carriage and at the other end to the first drive nut; and a second drive link pivoted at one end to the second carriage and at the other end to the second drive nut.

5. A controlled-immersion inspection mechanism, according to claim 4, in which the rotary motor is an electric motor, and in which the platform drive includes an energizing circuit for energizing the motor.

6. A controlled-immersion inspection mechanism, according to claim 5, in which the energizing circuit for the electric motor includes a limit switch to interrupt energization of the electric motor when the platform reaches one of its inspection and entry positions.

7. A controlled-immersion inspection mechanism, according to claim 6, in which the energizing circuit includes a first limit switch to interrupt energization of the electric motor when the platform reaches its inspection position and a second limit switch to interrupt energization of the electric motor when the platform reaches its entry position.

8. A controlled-immersion inspection mechanism, according to claim 1, in which the liquid medium in the tank is water.

9. A controlled-immersion inspection mechanism, according to claim 1, and further comprising:

a screen covering the articles on the platform to retain the articles in their orderly pattern during immersion as the platform moves from its entry position to its inspection position.

10. A controlled-immersion inspection mechanism, according to claim 1, in which the controlled-immersion inspection mechanism is an integral part of a scanning inspection apparatus.

11. A controlled-immersion inspection mechanism, according to claim 1, in which the controlled-immersion inspection mechanism is an integral part of a scanning acoustic microscope.

12. A method of inspecting a plurality of articles comprising the steps of:

A) filling a tank to a given level with a liquid medium;

B) arranging the articles in an orderly planar pattern;

C) moving the planar pattern of articles into the tank, along a path at an acute angle to the given surface level, from an entry position above the given level to an inspection position in which the pattern of articles is immersed in the liquid medium, parallel to but at a predetermined level below the given level; and D) scanning the articles, in the inspection position, with a beam of scanning energy, in accordance with a preselected scanning pattern correlated with the planar pattern of the articles.

13. A method of inspecting a plurality of articles, according to claim 12, and comprising the following additional step:

E) removing the articles from the tank, to a withdrawal position above the given surface level, free of the liquid medium.

14. A method of inspecting a plurality of articles, according to claim 12, and comprising the following additional steps subsequent to step C and prior to step D:

W) covering the planar pattern of articles with an open mesh.

15. A method of inspecting a plurality of articles, according to claim 12, in which, in step B, the articles are disposed on a planar surface of a support tray and remain on that planar tray surface throughout steps C, D, and E.

16. A method of inspecting a plurality of articles, according to claim 12, in which, in step D, test articles are scanned by a beam of ultrasonic energy.

17. A method of inspecting a plurality of articles, according to claim 16, in which the liquid medium is water.

18. A method of inspecting a plurality of articles, according to claim 12, in which the acute angle of step C is less than 30° C.

19. A method of inspecting a plurality of articles, according to claim 12, in which the acute angle of step C is approximately 10° C.

20. A method of inspecting a plurality of articles, according to claim 12, in which, during step C, the movement of the planar pattern of articles to the inspection position is a jogging movement to minimize formation of air bubbles or release air bubbles adjacent to the articles.

* * * * *